US007709685B2

(12) United States Patent
Hoshino et al.

(10) Patent No.: US 7,709,685 B2
(45) Date of Patent: *May 4, 2010

(54) METHOD FOR PRODUCING CYCLOALKANOL AND/OR CYCLOALKANONE

(75) Inventors: Masahiro Hoshino, Ehime (JP); Tatsuya Suzuki, Ehime (JP); Hajime Ishida, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/048,258

(22) Filed: Mar. 14, 2008

(65) Prior Publication Data
US 2008/0228007 A1    Sep. 18, 2008

(30) Foreign Application Priority Data
Mar. 16, 2007   (JP)  .............................. 2007-068045
Aug. 20, 2007   (JP)  .............................. 2007-213417

(51) Int. Cl.
*C07C 45/32* (2006.01)
*C07C 35/08* (2006.01)

(52) U.S. Cl. ...................................... 568/357; 568/822

(58) Field of Classification Search ................. 568/357, 568/822
See application file for complete search history.

(56) References Cited

U.S. PATENT DOCUMENTS 6,806,390 B1   10/2004   Herron et al.
2007/0225526 A1   9/2007   Hoshino

FOREIGN PATENT DOCUMENTS

EP   1 829 852 A1   9/2007
WO   WO 00/03963 A1   1/2000

OTHER PUBLICATIONS

Carvalho et al. Iron and Copper immobilised on mesoporous MCM-41 molecular sieves as catalysts for the oxidation of cyclohexane. Journal of Molecular Catalysis A: Chemical, 1999, vol. 144, pp. 91-99.*
Kurusu et al. Functionalization of Silica Gel: Application for the Catalytic Oxidation of Alkanes. Journal of Organic Chemistry, 1991, vol. 56, pp. 1981-1983.*
G. Lu$^a$, et al. "Gold nanoparticles in mesoporous materials showing catalytic selective oxidation cyclohexane using oxygen", Applied Catalysis A: General 280, (2005), pp. 175-180.
S. Liu, et al. "Liquid-Phase Oxidation of Cyclohexane Using Co-P-MCM-41 Catalyst", Korean J. Chem. Eng., 15(5), 1998, pp. 510-515.
Maschmeyer T. et al, "Designing a solid catalyst for the selective low-temperature oxidation of cyclohexane to cyclohexanone", Angewandte Chemie International Edition English, vol. 36, No. 15, 1997, pp. 1639-1642, XP002533872.
Selvam, P et al., "Transition-metal (Ti, V, Cr, Mn, Fe, Co, Cu) containing ordered nanoporous materials: novel heterogeneous catalysts for selective oxidation reactions", Journal of Nanoscience and Nanotechnology, American Scientific Publishers, US, vol. 6, No. 6, Jun. 1, 2006, pp. 1758-1764, XP009110478.
Tshavhungwe, A. M. et al., "Cobalt ion incorporation into periodic mesoporous organosilica materials synthesized by co-condensation of 1,2-bistrimethoxysilylethane with 3-glycidoxypropyltriethoxysilane", Journal of Sol-Gel Science and Technology, Springer, New York, NY, US, vol. 29, No. 3, Mar. 1, 2004, pp. 167-177, XP001199934.
Tatsumi T. et al, "Remarkable activity enhancement by trimethylsilylation in oxidation of alkenes and alkanes with $H_2O_2$ catalyzed by titanium-containing mesoporous molecular sieves", Chemical Communication, 1998, pp. 325-326, XP002533873.

* cited by examiner

*Primary Examiner*—Sikarl A Witherspoon
(74) *Attorney, Agent, or Firm*—Sughrue Mion, PLLC

(57) ABSTRACT

An object of the present invention is to provide a method capable of producing cycloalkanol and/or cycloalkanone with a favorable selectivity by oxidizing cycloalkane with a favorable conversion.

A cycloalkanol and/or cycloalkanone are produced by oxidizing cycloalkane with oxygen in the presence of mesoporous silica which contains at least one metal selected from metals of Groups 5 to 10 of the Periodic Table and which is also subjected to a contact treatment with an organosilicon compound. The metal is preferably at least one metal selected from the group consisting of vanadium, chromium, manganese, iron, cobalt, ruthenium and palladium, and the mesoporous silica is preferably MCM-41 type mesoporous silica.

6 Claims, 3 Drawing Sheets

METHOD FOR PRODUCING CYCLOALKANOL AND/OR CYCLOALKANONE

BACKGROUND OF THE INVENTION

1. Field of the Invention

The present invention relates to a method for producing cycloalkanol and/or cycloalkanone by oxidizing cycloalkane with oxygen.

2. Description of the Related Art

In a method for producing cycloalkanol and/or cycloalkanone by oxidizing cycloalkane with oxygen, a method of performing the oxidation reaction using mesoporous silica containing a certain kind of metal element as a catalyst has been studied. For example, there are known a method using mesoporous silica containing gold (Applied Catalysis A: General, Netherlands, 2005, Vol. 280, pp. 175-180), a method using mesoporous silica containing cobalt (Korean Journal of Chemical Engineering, Republic of Korea, 1998, Vol. 15, pp. 510-515), and a method using mesoporous silica containing chromium or vanadium (International Publication No. WO00/03963).

SUMMARY OF THE INVENTION

The above-mentioned conventional methods sometimes include unsatisfactory points in view of activity and selectivity of a catalyst, namely, the conversion of cycloalkane and the selectivity of cycloalkanol and/or cycloalkanone. Thus, an object of the present invention is to provide a method capable of producing cycloalkanol and/or cycloalkanone with a favorable selectivity by oxidizing cycloalkane with a favorable conversion.

The present inventors have intensively studied and found that the above object can be achieved by performing the above oxidation reaction in the presence of mesoporous silica which contains a predetermined metal and which is also subjected to a contact treatment with an organosilicon compound. Thus, the present invention has been completed.

The present invention provides a method for producing cycloalkanol and/or cycloalkanone, which comprises oxidizing cycloalkane with oxygen in the presence of mesoporous silica which contains at least one metal selected from metals of Groups 5 to 10 of the Periodic Table and which is also subjected to a contact treatment with an organosilicon compound.

According to the present invention, cycloalkanol and/or cycloalkanone can be produced with a favorable selectivity by oxidizing cycloalkane with a favorable conversion.

DETAILED DESCRIPTION OF THE INVENTION

Figure 1:
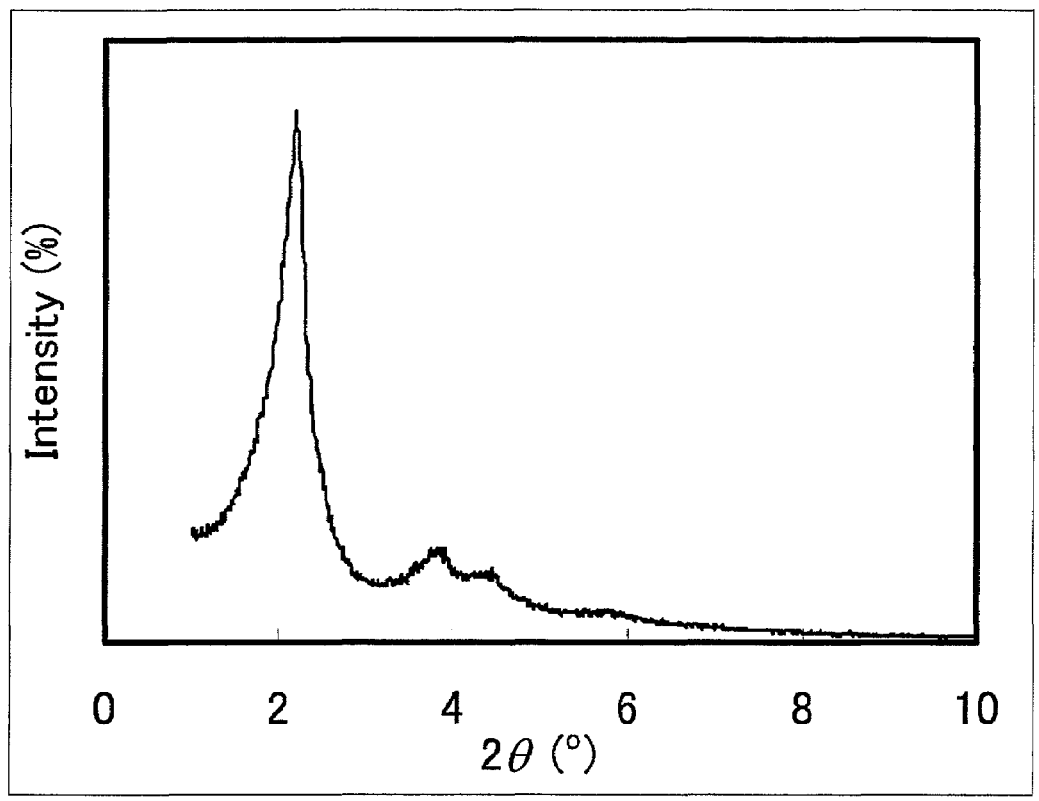
FIG. 1 is a graph showing an XRD pattern of the cobalt-containing mesoporous silica obtained in Reference Example 1.

The present invention will now be described in detail. In the present invention, the corresponding cycloalkanol and/or cycloalkanone is/are produced by oxidizing cycloalkane used as a starting material with oxygen (molecular oxygen) in the presence of a predetermined mesoporous silica.

Examples of the cycloalkane as the raw material include monocyclic cycloalkanes having no substituent on the ring, such as cyclopropane, cyclobutane, cyclopentane, cyclohexane, cycloheptane, cyclooctane, cyclodecane, or cyclooctadecane; polycyclic cycloalkanes such as decalin or adamantane, and cycloalkanes having a substituent on the ring, such as methylcyclopentane or methylcyclohexane, and also two or more kinds of them can be used, if necessary.

An oxygen-containing gas is usually used as the oxygen source. This oxygen-containing gas may be, for example, air, pure oxygen, or an air or pure oxygen diluted with an inert gas such as nitrogen, argon or helium. Oxygen enriched air obtained by adding pure oxygen to air can also be used.

In the present invention, the above oxidation reaction is performed in the presence of mesoporous silica which contains at least one metal selected from metals of Groups 5 to 10 of the Periodic Table and which is also subjected to a contact treatment with an organosilicon compound. When such mesoporous silica is used, cycloalkanol and/or cycloalkanone can be produced with a favorable selectivity by oxidizing cycloalkane with a favorable conversion.

Examples of the metal to be contained in the mesoporous silica include metals of Groups 5 to 10 of the Periodic Table, and are preferably vanadium, chromium, manganese, iron, cobalt, ruthenium and palladium. Among these metals, cobalt is preferable. If necessary, two or more kinds of these metals may be used. The content of the metal is usually from 0.01 to 20%, preferably from 0.05 to 10%, and still more preferably from 0.1 to 5%, in terms of a weight ratio of the metal to the mesoporous silica.

The mesoporous silica in the present invention has a so-called mesoporous structure containing pores which usually have a nearly uniform size of 2 to 50 nm, and the surface area thereof is usually from about 600 to 1,500 m$^2$/g. The metal may be incorporated into a silica framework constituting the mesoporous structure, or may be incorporated into the pores, or may be supported on the surface of the silica framework. Examples of the mesoporous silica include a MCM-41 type mesoporous silica, a MCM-48 type mesoporous silica, a FSM-16 type mesoporous silica, a SBA-15 type mesoporous silica and a HMS type mesoporous silica, among which a MCM-41 type mesoporous silica is preferable. The presence or absence of the mesoporous structure can be confirmed by the presence or absence of a peak 2θ=0.2 to 4.0° in the measurement of XRD (X-ray diffraction) using a copper Kα ray.

The mesoporous silica in the present invention is subjected to a contact treatment with an organosilicon compound. The organosilicon compound can be preferably reacted with the mesoporous silica to bond on the surface, and can be typically represented by the following formula (1):

$$Si(R^1)_x(R^2)_{4-x} \tag{1}$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

Examples of the alkoxy group represented by $R^1$ and $R^2$ include a methoxy group, an ethoxy group, a propoxy group and a butoxy group, and examples of the alkyl group represented by $R^2$ include a methyl group, an ethyl group, a propyl group and a butyl group. Examples of the aryl group represented by $R^2$ include a phenyl group, a naphthyl group and a tolyl group, and examples of the aralkyl group represented by $R^2$ include a benzyl group and a phenethyl group.

As the organosilicon compound represented by the formula (1), trialkoxyalkylsilane and tetraalkoxysilane are more preferably used.

The method for preparing the mesoporous silica will now be described. The silica having a mesoporous structure can be prepared by known methods described in Korean Journal of Chemical Engineering), Republic of Korea, 1998, Vol. 15, pp. 510-515, and Nature, U.S.A., 1992, Vol. 359, pp. 710-712. For example, the silica can be prepared by mixing tetraalkoxysilane such as tetraethoxysilane (ethyl orthosilicate), a quaternary ammonium salt such as hexadecyltrimethylammonium bromide, an alkali metal hydroxide such as sodium hydroxide, and water, and heat-treating the mixture at about 80 to 100° C., followed by filtration, drying and further calcining at about 500 to 600° C.

Examples of the method of incorporating the metal into the silica having a mesoporous structure include a method of adding a metal compound such as a halogenate, a nitrate, a carboxylate or an oxo-acid salt of the metal to the mixture in the process for preparation of the silica having a mesoporous structure; a method of impregnating the silica having a mesoporous structure with a solution of the above metal compound; a method of immersing the silica having a mesoporous structure in a solution of the metal compound thereby adsorbing the metal compound to the silica; and a method of ion-exchanging a metal cation of the metal compound with a cation of the silica. The amount of the metal compound used is appropriately adjusted so as to control to the content of the metal.

The method of subjecting to a contact treatment with an organosilicon compound includes, for example, a method of immersing the silica having a mesoporous structure, which does or does not contain the metal, in a liquid containing an organosilicon compound; and a method of bringing a gas containing an organosilicon compound into contact with the silica having a mesoporous structure, which does or does not contain the metal.

When the silica having a mesoporous structure without such metal is subjected to the contact treatment, it is possible to incorporate the metal similar to above by impregnating the silica subjected to the contact treatment with a solution of the metal compound, or immersing the silica subjected to the contact treatment in a solution of the metal compound.

The amount of the organosilicon compound used is usually from 1 to 10,000 parts by weight, preferably from 5 to 2,000 parts by weight, and more preferably from 10 to 1,500 parts by weight, based on 100 parts by weight of the silica before being subjected to the contact treatment.

The temperature of the contact treatment is usually from 0 to 300° C., and preferably from 30 to 250° C. The time for the contact treatment is usually from 0.1 to 50 hours, and preferably from 1 to 20 hours.

Thus, the mesoporous silica, which contains the above metal and is also subjected to a contact treatment with an organosilicon compound, can be obtained. Then, cycloalkane is oxidized with oxygen in the presence of the mesoporous silica. The amount of the mesoporous silica used is usually from 0.01 to 50 parts by weight, and preferably from 0.1 to 10 parts by weight, based on 100 parts by weight of the cycloalkane.

The reaction temperature is usually from 0 to 200° C., and preferably from 50 to 170° C., and the reaction pressure is usually from 0.01 to 10 MPa, and preferably from 0.1 to 2 MPa. A reaction solvent can be optionally used and, for example, nitrile solvents such as acetonitrile or benzonitrile, and carboxylic acid solvents such as acetic acid or propionic acid can be used.

A post-treatment after the oxidation reaction is not specifically limited and examples thereof include a method of filtering the reaction mixture thereby separating the catalyst, followed by washing with water and further distillation. When cycloalkyl hydroperoxide corresponding to the cycloalkane as the starting material is contained in the reaction mixture, it can be converted into the objective cycloalkanol and cycloalkanone by alkali treatment or reduction treatment.

EXAMPLES

Hereinafter, the present invention is described by reference to the Examples, but the present invention is not limited thereto. Cyclohexane, cyclohexanone, cyclohexanol and cyclohexyl hydroperoxide in the reaction solution were analyzed by gas chromatography, and the conversion of cyclohexane as well as each selectivity of cyclohexanone, cyclohexanol and cyclohexyl hydroperoxide was calculated from the analysis results.

Reference Example 1

Figure 2:
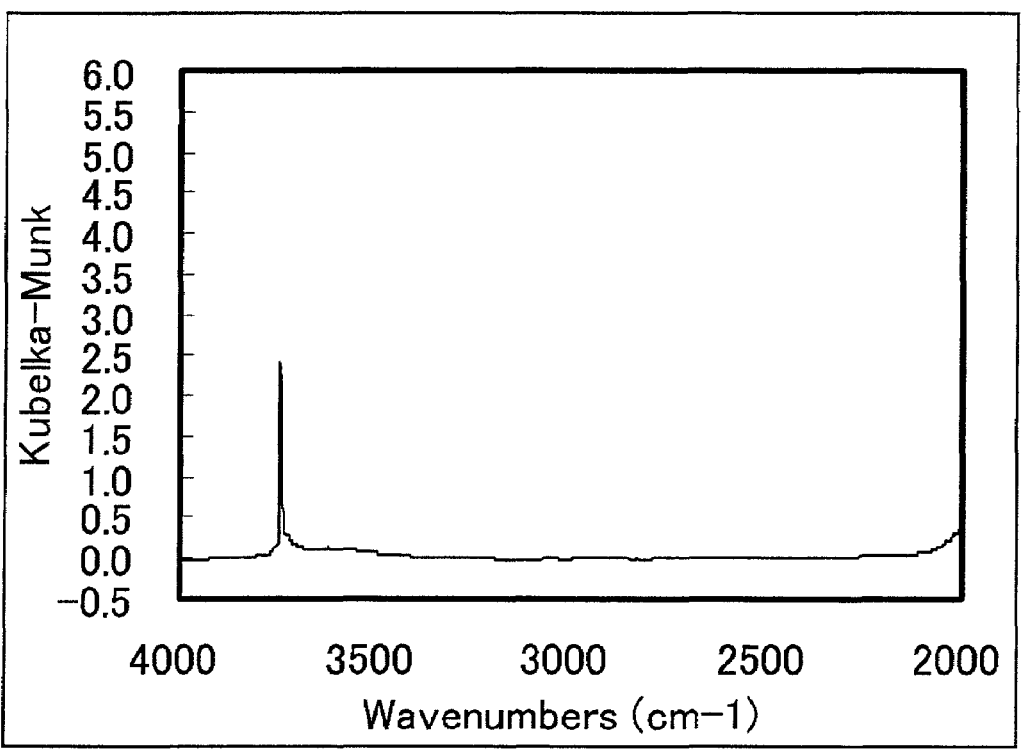
FIG. 2 is a graph showing an infrared absorption spectrum of the cobalt-containing mesoporous silica obtained in Reference Example 1.

Preparation of Cobalt-Containing Mesoporous Silica 8.08 g of hexadecyltrimethylammonium bromide (manufactured by Wako Pure Chemical Industries, Ltd.), 107.44 g of water, 1.63 g of sodium hydroxide (manufactured by Wako Pure Chemical Industries, Ltd.), 30.48 g of tetraethoxysilane (ethyl orthosilicate, manufactured by Wako Pure Chemical Industries, Ltd.) and 1.84 g of cobalt(II) acetate tetrahydrate (manufactured by Wako Pure Chemical Industries, Ltd.) were charged in a 200 ml beaker, stirred at room temperature for one hour and then hydrothermally synthesized at 90° C. for 7 days. The resulting mixture was filtered, and the residue was washed with water and then dried at 100° C. for 12 hours. The resulting dried product was calcined under an air flow at 550° C. for 7 hours. With respect to the powder obtained by calcination, XRD measurement was conducted using a copper Kα ray. As a result, it was confirmed that a peak peculiar to a mesoporous structure is observed at about $2\theta=2.3°$ and a cobalt-containing mesoporous silica is produced. The XRD pattern is shown in FIG. 1. An infrared absorption spectrum of the resulting cobalt-containing mesoporous silica was measured by the following procedure. The results are shown in FIG. 2.

Measurement of Infrared Absorption Spectrum

The cobalt-containing mesoporous silica obtained in Reference Example 1 was charged in a catalytic cell (Diffuse Reflectance Heat Chamber, Model HC900, manufactured by SPECTRA-TECH Co.) and set in an apparatus for measuring an infrared absorption spectrum (Magna 760-ESP, manufactured by NICOLET Co.) and, after deaeration under 0.1 Torr (13 Pa) at 200° C. for one hour, an infrared absorption spectrum was measured. The measuring conditions are as follows: the measuring temperature is 200° C., the measuring pressure is 0.1 Torr (13 Pa), the measuring range is from 400 to 4,000 cm$^{-1}$, and the resolution is 4 cm$^{-1}$. Using data obtained by measuring an infrared absorption spectrum of potassium bromide in the same manner as a background, the resulting data were subjected to Kubelka-Munk conversion.

Reference Example 2

Contact Treatment of Cobalt-Containing Mesoporous Silica with Triethoxyethylsilane 0.3 g of the cobalt-containing mesoporous silica obtained in Reference Example 1 and 3.0 g of triethoxyethylsilane (manufactured by Tokyo Kasei Kogyo Co., Ltd.) were charged in a flask and then stirred under a nitrogen atmosphere at 90° C. for 7.5 hours. The resulting mixture was cooled to room temperature and ethanol was added, followed by stirring and further filtration. The residue was washed with ethanol, dried under 0.1 Torr (13 Pa) at 40° C. for one hour and then dried at 100° C. An infrared absorption spectrum of the resulting cobalt-containing mesoporous silica subjected to a contact treatment with triethoxyethylsilane was measured in the same manner as in Reference Example 1. The results are shown in FIG. 3.

Figure 3:
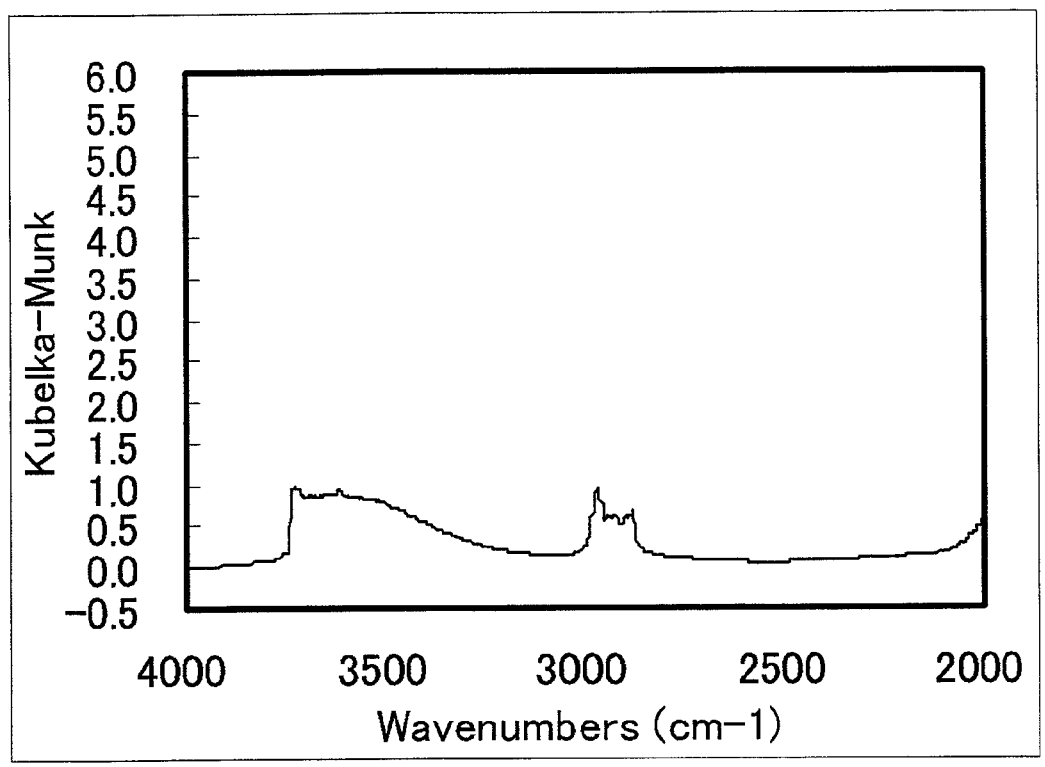
FIG. 3 is a graph showing an infrared absorption spectrum of the cobalt-containing mesoporous silica subjected to a contact treatment with triethoxyethylsilane obtained in Reference Example 2.

As shown in FIG. 2, a peak attributed to a so-called terminal silanol group is observed at about 3,740 cm$^{-1}$ in the cobalt-containing mesoporous silica obtained in Reference Example 1, while, as shown in FIG. 3, the same peak is not observed in the cobalt-containing mesoporous silica subjected to a contact treatment with triethoxyethylsilane obtained in Reference Example 2 and it is considered that the terminal silanol group is silylated with triethoxyethylsilane.

Reference Example 3

Contact Treatment of Cobalt-Containing Mesoporous Silica with Trimethoxypropylsilane 0.3 g of the cobalt-containing mesoporous silica obtained in Reference Example 1 and 3.0 g of trimethoxypropylsilane (manufactured by Tokyo Kasei Kogyo Co., Ltd.) were charged in a flask and then stirred under a nitrogen atmosphere at 90° C. for 7.5 hours. The resulting mixture was cooled to room temperature and ethanol was added, followed by stirring and further filtration. The residue was washed with ethanol, dried under 0.1 Torr (13 Pa) at 40° C. for one hour and then dried at 100° C. An infrared absorption spectrum of the resulting cobalt-containing mesoporous silica subjected to a contact treatment with trimethoxypropylsilane was measured in the same manner as in Reference Example 1. The results are shown in FIG. 4.

Figure 4:
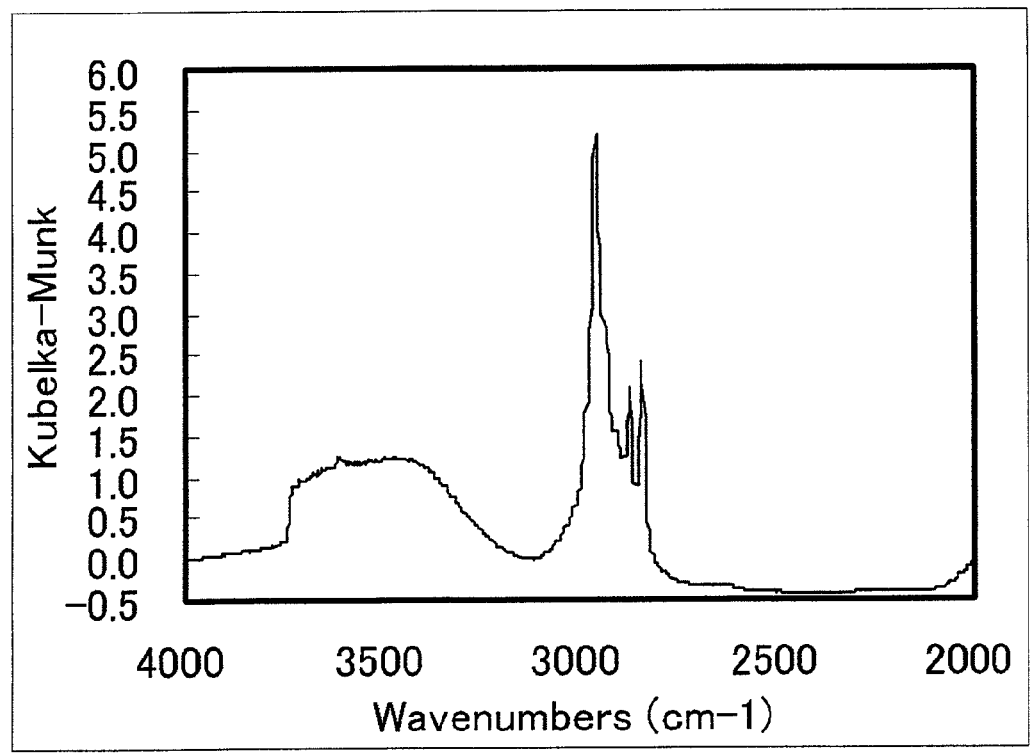
FIG. 4 is a graph showing an infrared absorption spectrum of the cobalt-containing mesoporous silica subjected to a contact treatment with trimethoxypropylsilane obtained in Reference Example 3.

As shown in FIG. 2, a peak attributed to a so-called terminal silanol group is observed at about 3,740 cm$^{-1}$ in the cobalt-containing mesoporous silica obtained in Reference Example 1, while, as shown in FIG. 4 the same peak is not observed in the cobalt-containing mesoporous silica subjected to a contact treatment with trimethoxypropylsilane obtained in Reference Example 3 and it is considered that the terminal silanol group is silylated with trimethoxypropylsilane.

Reference Example 4

Contact Treatment of Cobalt-Containing Mesoporous Silica with Tetraethoxysilane 0.3 g of the cobalt-containing mesoporous silica obtained in Reference Example 1 and 3.0 g of tetraethoxysilane (manufactured by Tokyo Kasei Kogyo Co., Ltd.) were charged in a flask and then stirred under a nitrogen atmosphere at 90° C. for 7.5 hours. The resulting mixture was cooled to room temperature and ethanol was added, followed by stirring and further filtration. The residue was washed with ethanol, dried under 0.1 Torr (13 Pa) at 40° C. for one hour and then dried at 100° C. An infrared absorption spectrum of the resulting cobalt-containing mesoporous silica subjected to a contact treatment with tetraethoxysilane was measured in the same manner as in Reference Example 1. The results are shown in FIG. 5.

Figure 5:
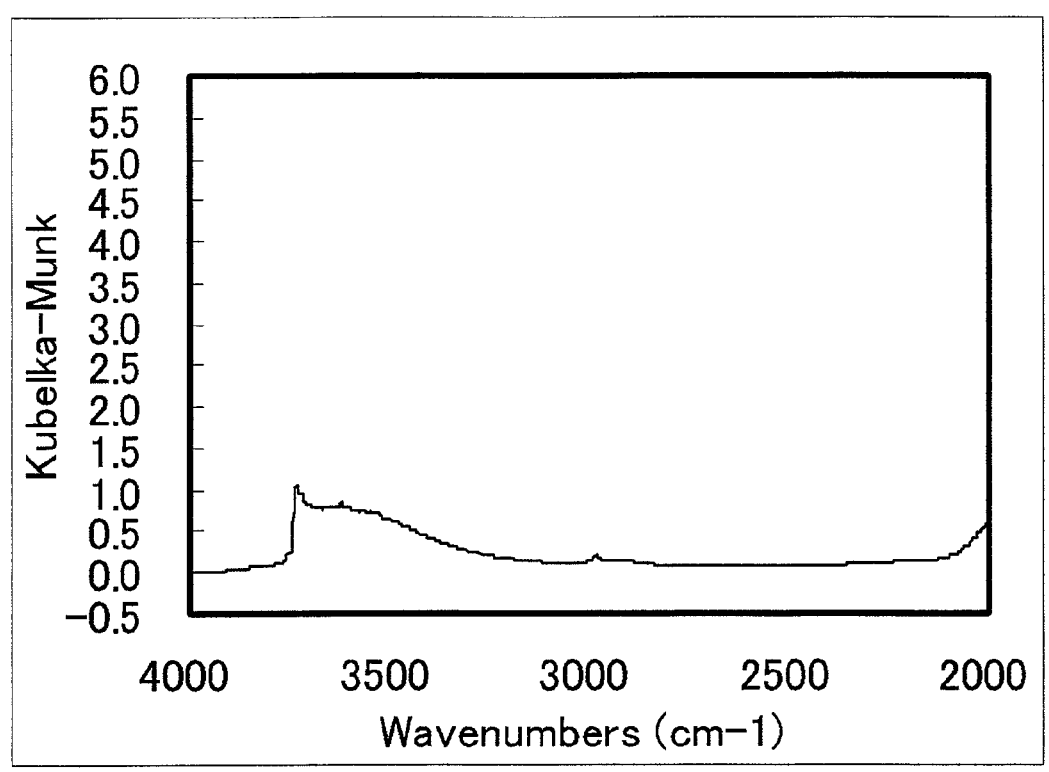
FIG. 5 is a graph showing an infrared absorption spectrum of the cobalt-containing mesoporous silica subjected to a contact treatment with tetraethoxysilane obtained in Reference Example 4.

As shown in FIG. 2, a peak attributed to a so-called terminal silanol group is observed at about 3,740 cm$^{-1}$ in the cobalt-containing mesoporous silica obtained in Reference Example 1, while, as shown in FIG. 5, the same peak is not observed in the cobalt-containing mesoporous silica subjected to a contact treatment with tetraethoxysilane obtained in Reference Example 4 and it is considered that the terminal silanol group is silylated with tetraethoxysilane.

Example 1

In a 300 ml autoclave, 100 g (1.2 mol) of cyclohexane and 0.1 g of the cobalt-containing mesoporous silica subjected to a contact treatment with triethoxyethylsilane obtained in Reference Example 2 were charged. After increasing the pressure in the system to 0.93 MPa at room temperature using nitrogen and heating to 130° C., the reaction was carried out under the flow of a gas having an oxygen concentration of 5 vol % for 8 hours.

5 hours after the beginning of the reaction, the conversion of cyclohexane was 7.5%, the selectivity of cyclohexanone was 36.8%, the selectivity of cyclohexanol was 47.9%, and the selectivity of cyclohexyl hydroperoxide was 2.2% (total selectivity: 86.9%). 8 hours after the beginning of the reaction (upon completion), the conversion of cyclohexane was 10.6%, the selectivity of cyclohexanone was 41.8%, the selectivity of cyclohexanol was 41.1%, and the selectivity of cyclohexyl hydroperoxide was 1.3% (total selectivity: 84.2%).

Example 2

The same operation as in Example 1 was conducted, except that the cobalt-containing mesoporous silica subjected to a contact treatment with trimethoxypropylsilane obtained in Reference Example 3 was used in place of the cobalt-containing mesoporous silica subjected to a contact treatment with triethoxyethylsilane obtained in Reference Example 2.

5 hours after the beginning of the reaction, the conversion of cyclohexane was 7.6%, the selectivity of cyclohexanone was 36.2%, the selectivity of cyclohexanol was 48.1%, and the selectivity of cyclohexyl hydroperoxide was 1.9% (total selectivity: 86.2%). 8 hours after the beginning of the reaction (upon completion), the conversion of cyclohexane was 10.8%, the selectivity of cyclohexanone was 41.2%, the selectivity of cyclohexanol was 41.7%, and the selectivity of cyclohexyl hydroperoxide was 1.2% (total selectivity: 84.1%).

Example 3

The same operation as in Example 1 was conducted, except that the cobalt-containing mesoporous silica subjected to a contact treatment with tetraethoxysilane obtained in Reference Example 4 was used in place of the cobalt-containing mesoporous silica subjected to a contact treatment with triethoxyethylsilane obtained in Reference Example 2.

5 hours after the beginning of the reaction, the conversion of cyclohexane was 7.5%, the selectivity of cyclohexanone was 36.5%, the selectivity of cyclohexanol was 47.6%, and the selectivity of cyclohexyl hydroperoxide was 1.4% (total selectivity: 85.5%). 8 hours after the beginning of the reaction (upon completion), the conversion of cyclohexane was 10.7%, the selectivity of cyclohexanone was 41.8%, the selectivity of cyclohexanol was 40.2%, and the selectivity of cyclohexyl hydroperoxide was 0.9% (total selectivity: 82.9%).

Comparative Example 1

The same operation as in Example 1 was conducted, except that the cobalt-containing mesoporous silica obtained in Reference Example 1 was used in place of the cobalt-containing silica subjected to a contact treatment with triethoxyethylsilane obtained in Reference Example 2.

5 hours after the beginning of the reaction, the conversion of cyclohexane was 7.4%, the selectivity of cyclohexanone was 35.8%, the selectivity of cyclohexanol was 47.2%, and the selectivity of cyclohexyl hydroperoxide was 1.3% (total selectivity: 84.3%). 8 hours after the beginning of the reaction (upon completion), the conversion of cyclohexane was 10.6%, the selectivity of cyclohexanone was 41.2%, the selectivity of cyclohexanol was 39.6%, and the selectivity of cyclohexyl hydroperoxide was 0.9% (total selectivity: 81.7%).

The major embodiments and the preferred embodiments of the present invention are listed below.

[1] A method for producing cycloalkanol and/or cycloalkanone, which comprises oxidizing cycloalkane with oxygen in the presence of mesoporous silica which contains at least one metal selected from metals of Groups 5 to 10 of the Periodic Table and which is also subjected to a contact treatment with an organosilicon compound.

[2] The method according to [1], wherein said at least one metal is selected from the group consisting of vanadium, chromium, manganese, iron, cobalt, ruthenium and palladium.

[3] The method according to [1], wherein said at least one metal is cobalt.

[4] The method according to any one of [1] to [3], wherein the mesoporous silica is MCM-41 type mesoporous silica.

[5] The method according to any one of [1] to [4], wherein the organosilicon compound is represented by the following formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

[6] The method according to any one of [1] to [4], wherein the organosilicon compound is trialkoxyalkylsilane or tetraalkoxysilane.

[7] A method according to any one of [1] to [6], wherein the cycloalkane is cyclohexane.

The present application has been filed claiming the priority based on Japanese Patent Applications No. 2007-068045 and No. 2007-213417, the entire contents of which are herein incorporated by reference.

What is claimed is:

1. A method for producing cycloalkanol and/or cycloalkanone, which comprises oxidizing cycloalkane with molecular oxygen in the presence of mesoporous silica which is obtained by subjecting a silica, having a mesoporous structure and containing at least one metal selected from metals of Groups 5 to 10 of the Periodic Table, to a contact treatment with an organosilicon compound represented by the following formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents an integer of 1 to 3.

2. The method according to claim 1, wherein said at least one metal is selected from the group consisting of vanadium, chromium, manganese, iron, cobalt, ruthenium and palladium.

3. The method according to claim 1, wherein said at least one metal is cobalt.

4. The method according to any one of claims 1 to 3, wherein the mesoporous silica is MCM-41 type mesoporous silica.

5. The method according to any one of claims 1 to 3, wherein the organosilicon compound is trialkoxyalkylsilane or tetraalkoxysilane.

6. The method according to any one of claims 1 to 3, wherein the cycloalkane is cyclohexane.

* * * * *